United States Patent [19]

Behar

[11] Patent Number: 4,528,981

[45] Date of Patent: Jul. 16, 1985

[54] CERVICAL IMMOBILIZATION DEVICE

[76] Inventor: Jean M. Behar, 4671 Dalebridge, Apt. No. 215, Warrensville Heights, Ohio 44128

[21] Appl. No.: 486,045

[22] Filed: Apr. 18, 1983

[51] Int. Cl.$^3$ ............................................. A61F 13/00
[52] U.S. Cl. ........................................ 128/133; 5/437
[58] Field of Search ...................... 128/69, 87 R, 87 B, 128/133, 134; 5/434, 436, 437

[56] References Cited

U.S. PATENT DOCUMENTS

| | | | |
|---|---|---|---|
| 2,952,856 | 9/1960 | Ruff | 5/437 |
| 3,174,163 | 3/1965 | Gibson | 5/437 |
| 3,672,364 | 6/1972 | Rankin | 128/134 |
| 3,719,185 | 3/1973 | Hanes | 4/436 |
| 3,897,777 | 8/1975 | Morrison | 128/133 |
| 4,034,748 | 7/1977 | Winner | 128/134 |
| 4,274,673 | 6/1981 | Kitterstein | 5/437 |
| 4,297,994 | 11/1981 | Bashaw | 128/133 |

*Primary Examiner*—Dalton L. Truluck
*Attorney, Agent, or Firm*—Fay, Sharpe, Fagan, Minnich & McKee

[57] ABSTRACT

A cervical immobilization device to be used in association with a stretcher or spine board for transport of an injured person and for restrainment of the head and spine portions against movement while resting on the board or stretcher is disclosed. A first weighted and resilient head support roll is provided having a general cylindrical configuration and sized for abutting contact against one head side portion and against an associated first shoulder portion. A second weighted and resilient head support roll is positioned opposite of the first roll and similarly has a generally cylindrical configuration and is sized for abutting contact against a second head side portion and against an associated second shoulder portion. Interconnecting means are provided for connecting the first head support roll to the second head support roll. The interconnecting means includes means for fixing the position of the first and second head rolls relative to the head and shoulder portions. The interconnecting means preferably comprise a plurality of flexible straps and the means for fixing preferably comprises an interlocking hook and loop fastening fabric being positioned on the straps and about the periphery of the head rolls.

5 Claims, 5 Drawing Figures

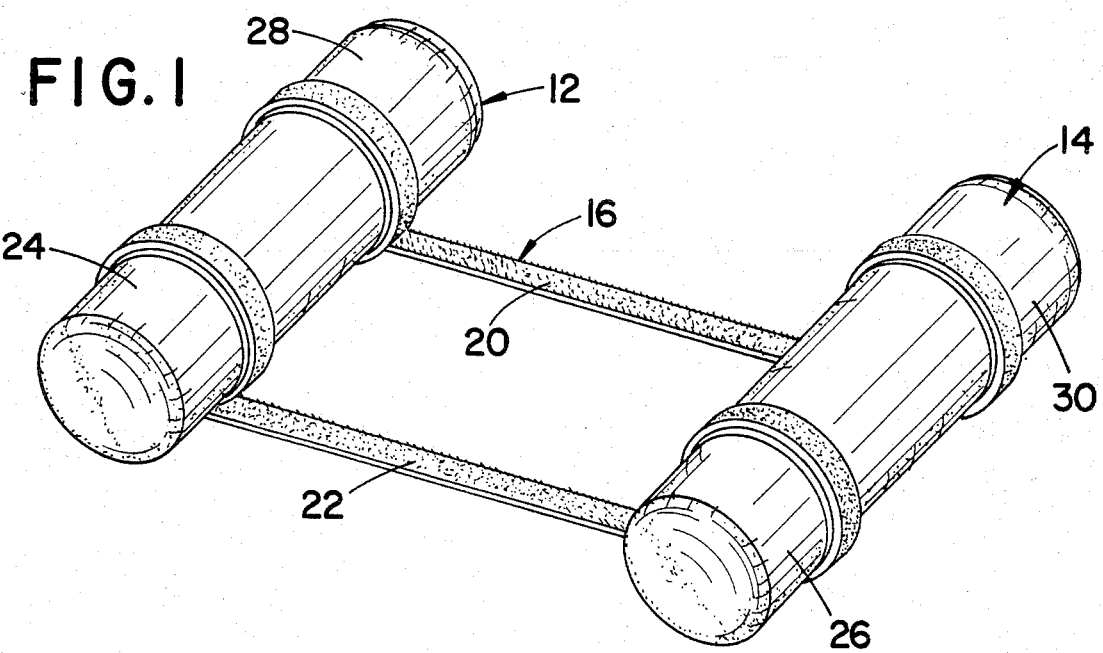
FIG. 1
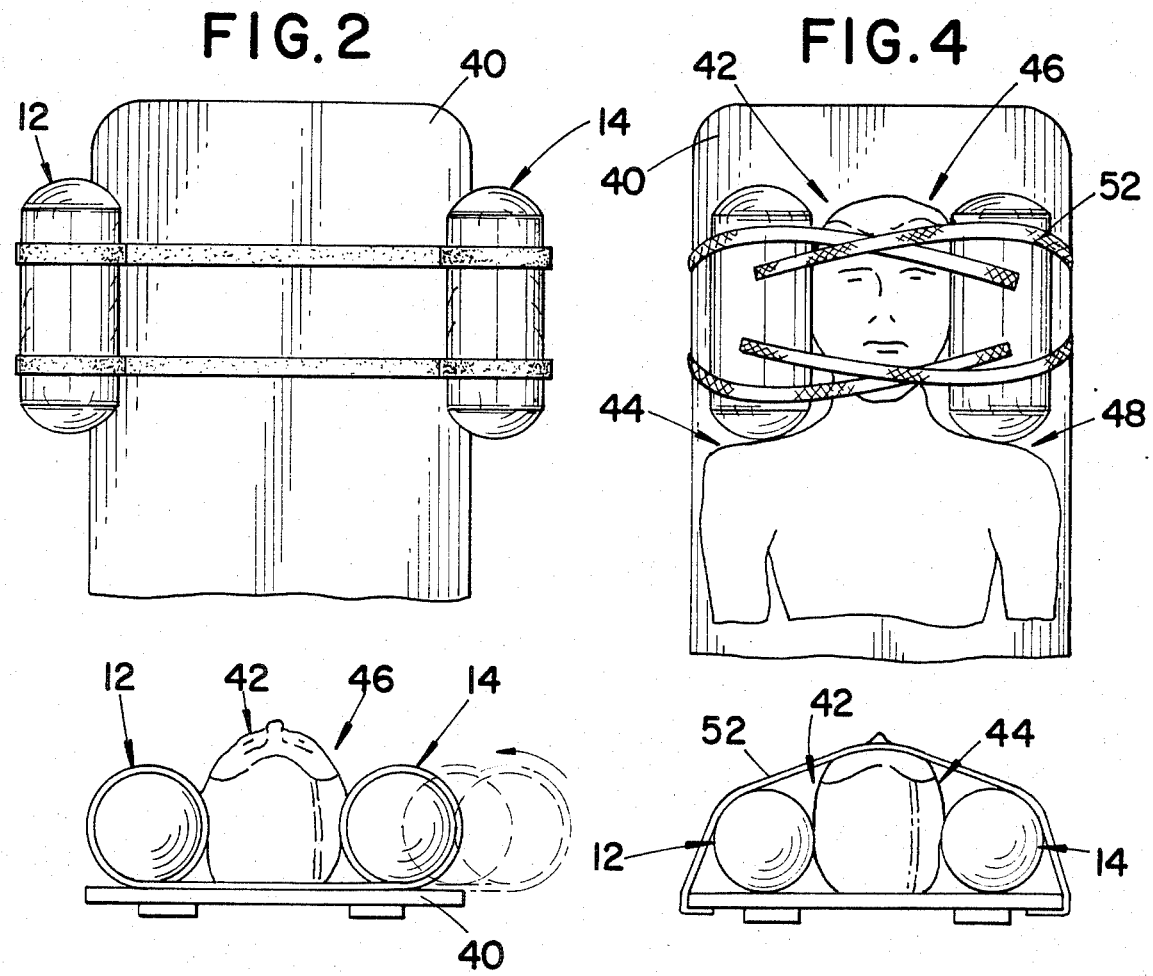
FIG. 2
FIG. 4
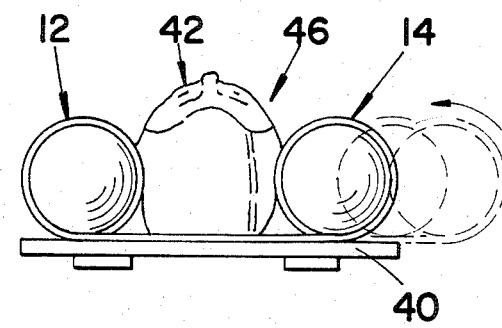
FIG. 3
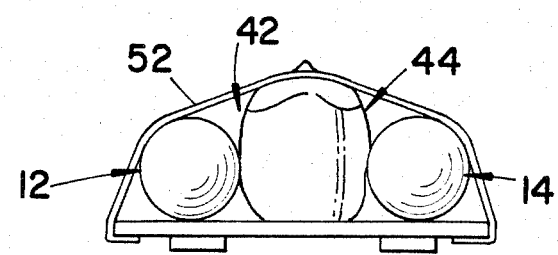
FIG. 5

CERVICAL IMMOBILIZATION DEVICE

BACKGROUND OF THE INVENTION

This invention pertains to the art of medical restraining or bracing devices and more particularly to a device for restraining the head of an injured person against movement while resting on a spine board.

In many accidents which involve severe physical harm to a person, spinal injuries are often overshadowed by more obvious and gruesome injuries such as bone fractures, skin lacerations and chest injuries. Since a spinal injury is an internal injury, ambulance and rescue personnel often have trouble identifying spinal injuries and, if identified, they are usually treated after the more obvious wounds have been treated and the person has been moved. However, any such spinal injury is usually compounded by movement or adjustment of the injured spine, thereby causing more permanent and irreparable damage.

Spinal cord injuries cannot always be corrected by surgery. In addition, the spinal cord has extremely limited self-healing powers. Thus it is vital that a rescuer to an injured person be able to immobilize known or suspected spinal fractures and dislocations quickly and correctly, since proper immobilization may be essential to obtain recovery and avoid paralysis or even death.

It is a conventional practice among ambulance and rescue personnel to rigidly immobilize conscious and unconscious accident victims having a known or suspected spinal injury. Such immobilization typically occurs by lashing the patient to a short spine board with a later transfer to a longer spine board or immediate immobilization on a long spine board. In all instances though, the patient is firmly lashed in a face up position to the board. However, when a rescuer comes upon an accident where the victim has suffered severe injuries, the extra minutes spent or lashing the victim to the short spine board and then transferral to a long spine board, may be life threatening.

Other situations may require an undesirable amount of time for extrication of the accident victim from the accident such as in an automobile wreckage or where the short spine board might not fit. For these situations, it is conventional practice to place a cervical collar on the patient while extricating him from the accident wreckage and for placement onto a long spine board and more firm immobilization thereon.

The most commonly used method for cervical immobilization on the long spine board includes restraining the movement of the head with sand bags in association with a conventional cervical collar. It has been found that the defects present in such cervical immobilization devices are such that the devices themselves are of limited value.

Many times immobilizing sand bags are not sufficiently secured to the injured person or the spine board and will move off of their proper position. In addition, since a sand bag is deformable but not elastomeric, the bags may be deformed away from their proper molded positions about the head and allow potentially further damaging movement to the head and spine.

Other known restraining devices such as are disclosed in U.S. Pat. No. 3,672,364; U.S. Pat. No. 4,034,748; U.S. Pat. No. 4,124,908; and British Pat. No. 436,549 suffer the more common problem of having a head immobilization device which is limited in its ability to be positioned relative to the head of an injured party by interconnecting members between the restraining devices and the associated spine board. Thus it is necessary to properly position the injured party relative to the restraining device and spine board for proper restrainment. This is a particular disadvantage because such a procedure often requires inconvenient movement of the injured person to obtain the proper position proper to use of the restraining devices.

The present invention contemplates a new and improved cervical immobilization device which overcomes the above referred to problems and others to provide a new cervical immobilization device which is simple in design, economical to manufacture, readily adaptable to a plurality of uses with spine boards having a variety of dimensional characteristics, easy to position, easy to remove and which provides improved immobilization to the spine of an injured person.

BRIEF SUMMARY OF THE INVENTION

In accordance with the present invention, there is provided a cervical immobilization device for restraining the head of an injured person against movement while resting on a spine board. The device comprises a first resilient head support roll, a second resilient head support roll and interconnecting means for connecting the first head roll to the second head support roll. The first resilient head support roll has a generally cylindrical configuration and is sized for abutting contact against one head side portion and against an associated first shoulder portion. The second resilient head support roll is positioned opposite of the first roll and has a generally cylindrical configuration and is sized for abutting contact against a second head side portion and against an associated second shoulder portion. The interconnecting means includes a means for fixing positions of the first and second head rolls relative to the head and shoulder portions. The interconnecting means preferably comprises a plurality of flexible straps. The straps are mounted to a base portion of the first head roll and the base portion of the second head roll and to a top portion of the first head roll and the top portion of the second head roll.

In accordance with another aspect of the present invention, the means for fixing the positions of the first and second head rolls relative to the head and shoulder portions comprises an interlocking hook and loop fastening fabric. The fabric is positioned on the straps and the head rolls.

In accordance with the present invention, there is also provided a method for restraining movement of the head of an injured person resting on a spine board. The method comprises placing the person on a spine board in a position where the head is interposed between the opposed first and second rolls of a cervical immobilization device configured in accordance with the present invention. The method further includes winding the first roll to a first fixed position defined by abutment of the first roll to a one head side portion and against an associated first shoulder portion. Next, winding the second roll to a second fixed position defined by abutment of the second roll to a second head side portion and against an associated second shoulder portion. The method further includes interfastening the rolls in the fixed position to the spine board and the head whereby the head is supported and restrained against damaging movement. The interfastening comprises applying adhesive tape segments to interconnect the rolls, spine board and head.

One benefit obtained by use of the present invention is a cervical immobilization device which is not restricted in a position relative to an associated spine board.

Another benefit obtained from the present invention is a cervical immobilization device which immobilizes the head and spine of an injured person relative to the shoulders of the person.

A further benefit of the present invention is a cervical immobilization device which is deformable and elastomeric to absorb potentially damaging movement and shock to an injured person restrained by the invention.

Other benefits and advantages for the subject new cervical immobilization device and method will become apparent to those skilled in the art upon a reading and understanding of this specification.

BRIEF DESCRIPTION OF THE DRAWINGS

The invention may take physical form in certain parts and arrangements of parts, the preferred embodiment of which will be described in detail in this specification and illustrated in the accompanying drawings which form a part hereof and wherein:

FIG. 1 is a perspective view of a cervical immobilization device formed in accordance with the present invention;

FIG. 2 is a plan view of the device of FIG. 1 positioned relative to a spine board prior to restraining of an injured person to be received on the spine board;

FIG. 3 is an end view of a spine board including a cervical immobilization device formed in accordance with the present invention and illustrating a step in the method of applying the invention for immobilization of the spine of an injured person;

FIG. 4 is a plan view of an injured person restrained in accordance with the device and method of the present invention; and, FIG. 5 is an end view of an injured person restrained in accordance with the method and device of the present invention.

DETAILED DESCRIPTION OF THE INVENTION

Referring now to the drawings wherein the showings are for purposes of illustrating the preferred embodiment of the invention only and not for purposes of limiting the same, the FIGURES show a cervical immobilization device 10 for restraining the head of an injured person against movement while resting on a spine board.

More specifically and with reference to FIGS. 1 and 2, immobilization device 10 includes a first resilient head support roll 12, a second resilient head support roll 14 and interconnecting means 16 for connecting the first head support roll to the second head support roll. Both the first and second head support rolls are generally cylindrically configured and sized for abutting contact against opposite head side portions of the injured person and against associated shoulder portions as will be hereinafter more fully discussed. The rolls are constructed of material firm enough to resist bending forces but soft and resilient enough for comfort of the patient. The rolls are resilient as opposed to being permanently deformable such as conventional immobilization sand bags. The rolls include a surface covering of waterproof material such as vinyl to facilitate removal and washing of blood and other fluids which may be designed on the rolls. The interconnecting means 16 preferably comprises a plurality of flexible straps 20, 22. At least one strap 22 is mounted to a base portion 24 of the first roll 12 and a base portion 26 of the second roll 14. Another strap 20 is mounted to a top portion 28 of the first roll 12 and a top portion 30 of the second roll 14. Although it is within the scope of the invention to include alternate arrangements of interconnecting straps.

The interconnecting means 16 includes a means for fixing the position of the first and second rolls 12, 14 relative to each other and the head and shoulder portions of an injured person to be restrained thereby. The means preferably comprises an interlocking hook and loop fastening fabric such as is sold under the trademark VELCRO. The fabric is positioned on the straps and about the periphery of the head rolls for locking engagement upon winding of the rolls within the straps.

With particular reference to FIGS. 2 through 5, the improved method and operation of the new cervical immobilization device will be specifically discussed.

The invention is to be used in association with a spine board 40 for restraining the head of an injured person resting on the spine board. The method comprises first placing an injured person on the spine board in a position wherein the head is interposed between the opposed first and second rolls 12, 14 of the invention. It is a feature of the invention that the injured person need not be placed in a particular lateral position between the rolls 12, 14, as the invention is adjustable to restrain the head and spine without regard to the exact position of the person on the spine board 40. The injured person is restrained by winding the first roll 12 to a first fixed position defined by abutment of the first roll 12 to a one head side portion 42 and against an associated first shoulder portion 44. The second roll is also wound to a second fixed position defined by abutment of the second roll 14 to a second head side position 46 and against an associated second shoulder portion 48 (FIG. 3). As the rolls are wound to their respective fixed positions, the interlocking hook and loop fastening fabric operates to lock the rolls 12, 14 in the desired fixed positions. After the rolls are wound to the proper positions, they are interfastened to the spine board 40 and the head of the injured party by preferably applying adhesive tape segments 52 to interconnect the rolls, spine board and head. When taping it is advantageous to adhere one end of a tape segment 52 to one roll and bring the other end of the segment 52 to the opposite roll and extend it beyond the roll and adhere the segment to the spine board 40, taping down both the forehead of the injured person and the other roll simultaneously. The tape should be crisscrossed on the forehead and chin area.

With the invention in place, the head of the injured person cannot move laterally due to the individual taping of each roll 12, 14 relative to the spine board 40. The head cannot be inclined relative to the shoulders since the rolls are resting on the associated shoulder positions to hold the head in a perpendicular position relative to the shoulders. Since each roll is individually taped to the spine board, the tape cannot slide off of the head of the patient no matter how diaphoretic the patient may be.

The cervical immobilization device should always be used in conjunction with a cervical collar (not shown).

The invention can be used with a plurality of stretchers and spine boards due to its freedom from the stretcher prior to the restrainment of the injured party.

The invention has been described with reference to the preferred embodiment. Obviously, modifications and alterations will occur to others upon a reading and understanding of the specification. It is my intention to include all such modifications and alterations insofar as they come within the scope of the appended claims or the equivalents thereof.

Having thus described my invention, I now claim:

1. A cervical immobilization device for restraining the head of an injured person against movement while resting on a spine board, said device comprising:

a first resilient head support roll, said first roll having a generally cylindrical configuration and sized for abutting contact against one head side portion and against an associated first shoulder portion;

a second resilient head support roll, opposite of said first roll, said second roll having a generally cylindrical configuration and sized for abutting contact against a second head side portion and against an associated second shoulder portion; and interconnecting means for connecting said first head support roll to said second head support roll comprising a plurality of flexible straps, at least one of said plurality mounted about a periphery of a base portion of said first head roll and a periphery of a base portion of said second head roll and at least one other of said plurality mounted about a periphery of a top portion of said first head roll and a periphery of a top portion of said second head roll, said straps including interlocking hook and loop fastening fabric positioned on said straps and said head rolls for fixing positions of said first and second head rolls relative to the head and shoulder portions by locking engagement of said straps to said head rolls upon winding of said head rolls into said straps.

2. A method for restraining movement of the head of an injured person resting on a spine board comprising:

placing the person on the spine board in a position wherein the head is interposed between opposed first and second rolls of a cervical immobilization device;

winding said first roll to a first fixed position defined by abutment of said first roll to a one head side portion and against an associated first shoulder portion;

winding said second roll to a second fixed position defined by abutment of said second roll to a second head side portion and against an associated second shoulder portion; said winding comprising rolling said rolls against associated interlocking hook and loop fastening fabric, said fabric being included on said rolls and extending from said first roll to said second roll.

3. The method as described in claim 2 wherein interfastening said rolls comprises applying adhesive tape segments to interconnect said rolls, spine board and head.

4. In a spinal restraint device for use in association with a stretcher for transport of an injured person, having a plurality of opposed weighted and resilient bags for restraining the head of the injured person, said bags including anchor straps interconnecting said bags to said stretcher and biasing said bags relative to the head, the improvement comprising:

a pair of opposed cervical immobilization rolls sized for restraining abutment against the head and shoulder of the injured person and interconnected with straps of interlocking hook and loop fastening fabric; said rolls further including said fabric about a periphery portion, said rolls and straps being free of said stretcher prior to restrainment of the injured party.

5. A cervical immobilization device for restraining the head of an injured person against movement while resting on a spine board, said device comprising:

first and second head support rolls including an interlocking hook and loop fastening fabric strap disposed about the periphery of said rolls and extending therebetween for locking engagement of said head rolls to said strap upon winding of said head rolls into said strap.

* * * * *